United States Patent [19]
Loori

[11] Patent Number: 4,801,291
[45] Date of Patent: Jan. 31, 1989

[54] PORTABLE TOPICAL HYPERBARIC APPARATUS

[76] Inventor: Phillip E. Loori, 912 Summit Ave., Jersey City, N.J. 07307

[21] Appl. No.: 122,355

[22] Filed: Nov. 18, 1987

[51] Int. Cl.$^4$ .............................................. A61M 37/00
[52] U.S. Cl. ...................................... 604/23; 604/289
[58] Field of Search ...................... 604/23, 24, 25, 289

[56] References Cited
U.S. PATENT DOCUMENTS

| | | | |
|---|---|---|---|
| 4,224,941 | 9/1980 | Stivala | 604/23 |
| 4,328,799 | 5/1982 | LoPiano | 128/207.26 |
| 4,474,571 | 10/1984 | Lasley | 604/23 |
| 4,624,656 | 11/1986 | Clark et al. | 604/23 |

OTHER PUBLICATIONS

Oxycure Promotional Materials, Concord Laboratories, Inc., Keene, New Hampshire 03431.
Oxycure Promotional Materials, Hospitak, Inc., Lindenhurst, New York, 11757.

Primary Examiner—Allen M. Ostrager
Attorney, Agent, or Firm—Lerner, David, Littenberg, Krumholz & Mentlik

[57] ABSTRACT

A topical hyperbaric apparatus and method is disclosed. The apparatus comprises a shell having at least one flexible wall portion which provides an external surface and defines a substantially closed internal chamber. The wall portion has an opening therethrough communicating with the internal chamber. The flexible wall portion is sufficiently flexible so as to be capable of conforming to an irregularly shaped surface of a patient's body. An adhesive sealing material is provided on the flexible wall portion for adhesively sealing the shell to the patient's body about the portion to be treated. A gas impermeable liner lines the internal chamber and makes the internal chamber substantially gas impermeable. Therapeutic gases are introduced into the internal chamber to therapeutically treat a portion of the patient's body encompassed by the opening.

42 Claims, 3 Drawing Sheets

PORTABLE TOPICAL HYPERBARIC APPARATUS

FIELD OF THE INVENTION

The present invention relates to hyperbaric chamber devices and, more particularly, to hyperbaric chamber devices which are portable, disposable and adapted for use in connection with irregular portions of the human body.

BACKGROUND OF THE INVENTION

Hyperbaric chambers are devices which create sealed environments for the application of therapeutic gases to hasten healing of lesions or wounds on a patient's body. The introduction of pressurized oxygen into such an encapsulated environment promotes healing of various types of lesions and wounds. Specifically, it has been discovered that the treatment of lesions and wounds with hyperbaric chambers, in conjunction with various stimuli, promotes granulation, raises the capillary blood $p^{02}$, elevates the Redox potential and suppresses bacterial proliferation. It has been determined that a constant pressure of 22–26 mmHG (1.03 atmospheres) and flow rates of 2 to 8 liters per minute are preferred. The introduction of humidity into hyperbaric chambers also produces positive results.

When hyperbaric chambers were first introduced they encompassed large portions of the patient's body. As time progressed, hyperbaric chambers became more sophisticated and topical hyperbaric chambers were developed. A topical hyperbaric chamber is a device which only encapsulates a small portion of the user's body. As these devices have evolved though, it has become apparent that significant shortcomings continue to exist.

These shortcomings include the failure of the art to provide a convenient portable hyperbaric unit, a portable hyperbaric unit which is capable of producing a hermetic seal in many applications, a portable hyperbaric unit which is affordable, and a portable hyperbaric unit which is disposable. The present invention provides advancements in these areas. In particular it is an object of the present invention to provide a topical hyperbaric apparatus capable of adapting to various contours of the human body. It is another object of the present invention to provide such an apparatus which is convenient to use and fully portable. A further object of the present invention is to provide such an apparatus at a cost which will enable wider use and, in the proper case, disposability; such disposability being a significant improvement and widely acknowledged as necessary in facilities which treat large numbers of patients.

Prior to the present invention, portable hyperbaric units were available, but these units failed to solve many of the presently addressed problems. For instance, in Lasley, U.S. Pat. No. 4,509,513, the patient is apparently required to stand during treatment. This is at times a sufficient enough requirement to preclude the use of this device. The '513 device is also constructed to encompass a large portion of the patient's body. This requires a relatively significant amount of oxygen and exposes areas of the body which do not require treatment to the negative effects of the therapeutic atmosphere, such as drying.

LoPiano, U.S. Pat. No. 4,328,799, discloses a device which treats only a small area of the patient's body and, therefore, solves the problem of unduly exposing healthy parts of the patient's body to the drying effects of the therapeutic atmosphere. However, this device fails to provide adequate seals during various applications. This poor sealing is significant because many of the areas of the body where such poor sealing occurs are areas which are highly susceptible to treatable lesions, such as bedsores on the buttock. This poor sealing is the result of both the inherent design of the device and movements of the patient. The inherent sealing limitations of this device result from the sealing apparatus which it utilizes. This sealing apparatus is in fact comprised of the patient's body, the bed frame or suitable other securing means and a feathered edge flange which expands and seals against the patient's body when the appropriate treating atmosphere is introduced into the chamber itself. This feathered flange is suited for producing a seal only on areas of the body which are basically flat. This device is not suitable for use in the area of bony protrusions or other irregularities in the surface of the skin, such as the division between buttock. This is a significant limitation.

Lasley, U.S. Pat. No. 4,474,571, discloses a portable topical hyperbaric chamber similar to the LoPiano patent. This device alleviates the need for cumbersome securing means by introducing a belting means in conjunction with a more resilient feathered flange sealing means. This device though, as discussed in relation to the '513 patent, similarly suffers from the shortcomings of the feathered flange sealing means; and similarly is only effective on portions of the body which do not exhibit surface irregularities. Accordingly, there is a need for an improved portable hyperbaric chamber which is capable of being effectively applied to the less easily treatable area of the human body. This is a significant need because, as previously stated, bedsores and the like typically occur in the non-planar areas of the human body.

SUMMARY OF THE PRESENT INVENTION

The present invention addresses the aforementioned problems. In accordance with one aspect of the present invention, an improved sealing apparatus is provided. More particularly, the hyperbaric apparatus includes a shell having at least one wall which provides an external surface and defines and internal chamber. An opening is provided through the wall which communicates with the internal chamber. Disposed on the external circumference of this opening is an adhesive sealing material which is adapted to adhesively seal this internal chamber to the patient's body. When this shell is thus affixed to the patient's body, there is provided a substantially closed internal chamber in communication with the area to be treated. There is also provided, and communicating with the substantially closed internal chamber, gas introduction means for introducing therapeutic gases into the chamber. Such gas introduction means allow for therapeutic gases, such as pressurized $O_2$, to be introduced within this chamber with the result of bringing such gases into contact with the portions of the patient's body to be treated.

In accordance with another aspect of the present invention, there is provided a hyperbaric apparatus having a shell which includes at least one wall providing an external surface and defining a substantially closed internal chamber within this shell. The at least one wall includes a substantially flexible portion capable of conforming to irregularly shaped surfaces of a patient's body, and has an opening therethrouqh which communicates with the internal chamber. Lining the internal chamber is a substantially gas impermeable material which in turn creates a gas impermeable internal chamber. There is also provided a gas introduction means which allows therapeutic gases, such as pressurized $O_2$, to be introduced within this chamber and in turn come into contact with the portions of the patient's body to be treated.

In addition to improved sealing means and flexible shell apparatus in the environment of hyperbaric chambers, the present invention also provides an improved method of therapeutically treating wounds and sores. More particularly, in accordance with this aspect of the present invention, the method comprises the steps of affixing a hyperbaric chamber apparatus to a patient's body through the use of an adhesive sealing means. The adhesive sealing means allows for attachment without pressurization or belting means, although such belting means may be used to further buttress such adhesive attachment. In accordance with another aspect of the present invention there is provided an improved method of application as a result of the flexibility of the hyperbaric chamber apparatus itself. In particular such flexibility enables a method of treatment wherein the hyperbaric chamber apparatus conforms to irregularly shaped portions of the patient's body and as a result seals the areas to be treated. This enables the treatment of wound sites heretofore effectively untreatable by existing devices.

In addition to the treatment of wound sites previously untreatable in the absence of a much more cumbersome device, numerous benefits flow from the present invention, such as portability, hermetic sealing in a portable device, and lower cost. Such lower cost in turn produces another set of benefits, such as wider availability and use, application in areas where it was previously economically inefficient, and disposability. Finally, such disposability in turn produces yet another set of benefits, such as reduction of "down time" per unit, reduction of sterilization needs and infection control.

BRIEF DESCRIPTION OF THE DRAWINGS

For a more complete understanding of the present invention, reference is made to the following detailed description of an exemplary embodiment considered in conjunction with the accompanying drawings in which.

DETAILED DESCRIPTION OF THE PREFERRED EMBODIMENT

Figure 1:
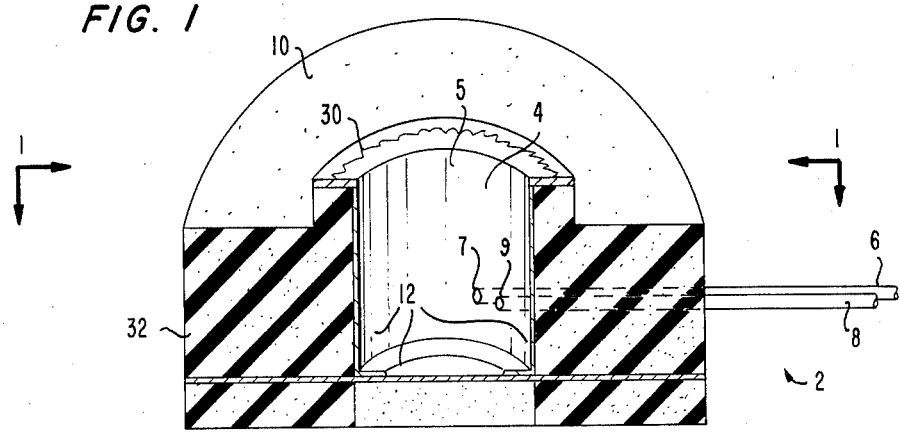
FIG. 1 is a perspective cross-sectional view of the hyperbaric chamber apparatus in accordance with the present invention taken along lines 1—1 of FIG. 2.

Referring now to the drawings, wherein like reference characters represent like elements, there is shown a preferred embodiment of a topical hyperbaric apparatus 2 in accordance with the present invention. As is conventional, hyperbaric apparatus 2 is to be applied to the patient's body for the treatment of various wounds and lesions. The hyperbaric apparatus 2 according to the present invention administers therapeutic gases to wound sites by creating a sealed internal chamber 4 which encapsulates such wound sites. When thus encapsulated, therapeutic gases are introduced, and the healing of such wounds is aided.

FIG. 1 illustrates a cross-sectional perspective view of the instant invention. Hyperbaric chamber apparatus 2 is here cut along line 1—1 of FIG. 2. Internal chamber 4 may be seen as residing in the middle of a shell 10 having an opening 5 disposed on one end. Gas introduction means 6 is seen passing through shell 10 and terminating at port 7. Pressure relief means 8 also passes through shell 10 and terminates at port 9. Ports 7 and 9 are sealably affixed to gas impermeable liner 12. Adhesive sealing means 30 is disposed about opening 5.

Figure 4:
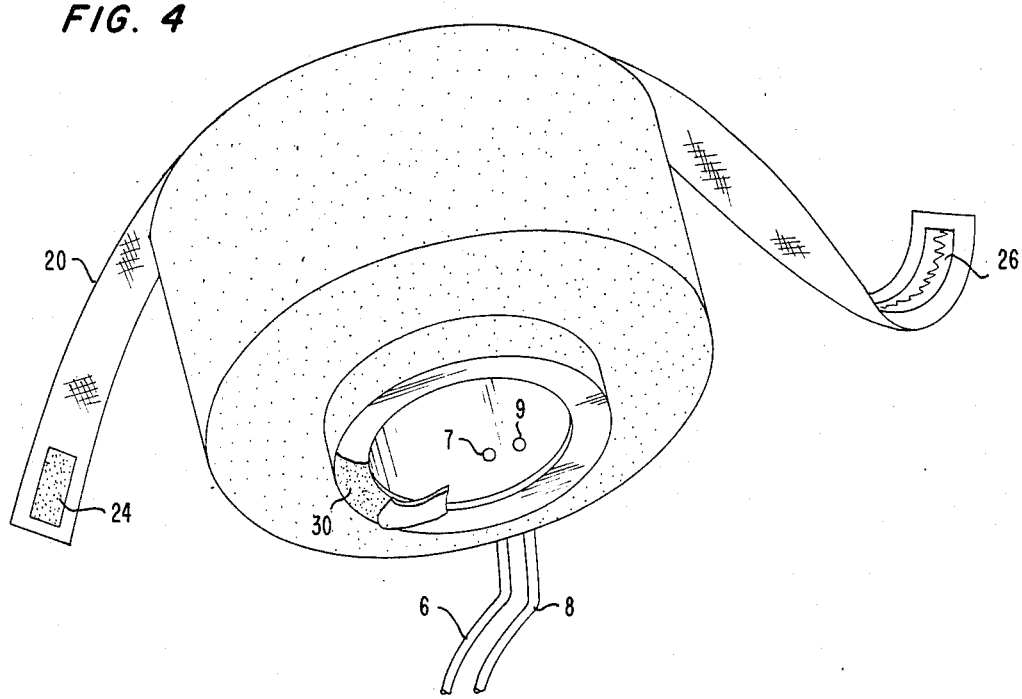
FIG. 4 is a bottom perspective view of the hyperbaric chamber apparatus in conjunction with belting means.

Belting means 20 may be provided as well, as best viewed in FIG. 4. Therein, hook affixing means 24 and loop fastening means 26 are also seen. Fastening means 26 is superimposed over the entire length of belt 20. Affixing means 24 is disposed only at one end.

The internal chamber 4 is sealed on top end 11 by gas impermeable liner 12. Gas impermeable liner 12 lines the inside of chamber 4 and, as stated, seals top end 11 of said chamber. This is best seen in FIG. 1, where gas impermeable liner 12 and shell 10 are cut along line 1—1.

Figure 2:
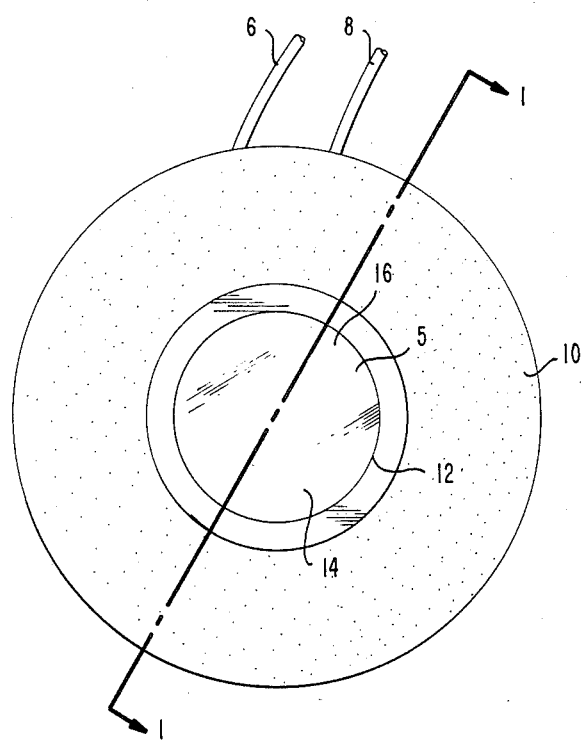
FIG. 2 is a bottom plan view of the hyperbaric chamber apparatus illustrated in FIG. 1.
Figure 3:
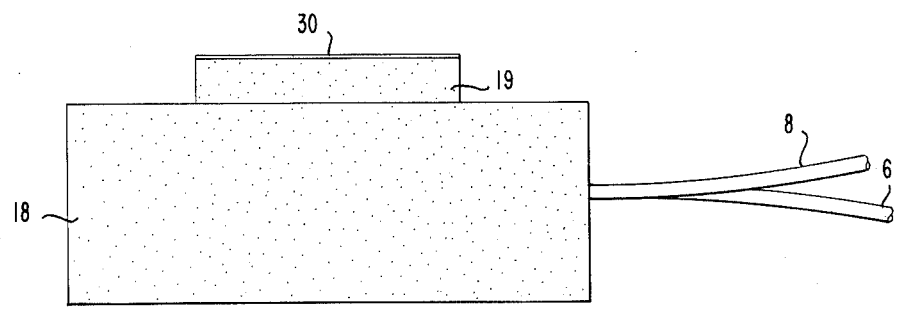
FIG. 3 is a side view of the hyperbaric chamber apparatus.

Referring now to FIG. 2, shell 10 as configured, is of a doughnut shape, with non-permeable liner 12 creating a cuplike structure or sealed chamber 14 within shell 10. The only passageways to such sealed chamber 14 are therapeutic gas introduction means 6, pressure relief means 8, and opening 5.

Shell 10 is comprised of a base 18 and a short protuberance 19 at the bottom end 16. Circumscribing and disposed on the edge of short protuberance 19 is adhesive sealing means 30. Adhesive sealing means 30, in conjunction with sealed chamber 14, when applied to the patient's body 1, creates an encapsulated area except for the passageways represented by ports 7 and 9, which are adapted to receive therapeutic gas introduction means 6, and pressure relief means 8, respectively. In use, therapeutic gas introduction means 6 is sealed by attachment to therapeutic gas source 40 and pressure relief means 8 is sealed by attachment to pressure release apparatus 50.

Figure 6:
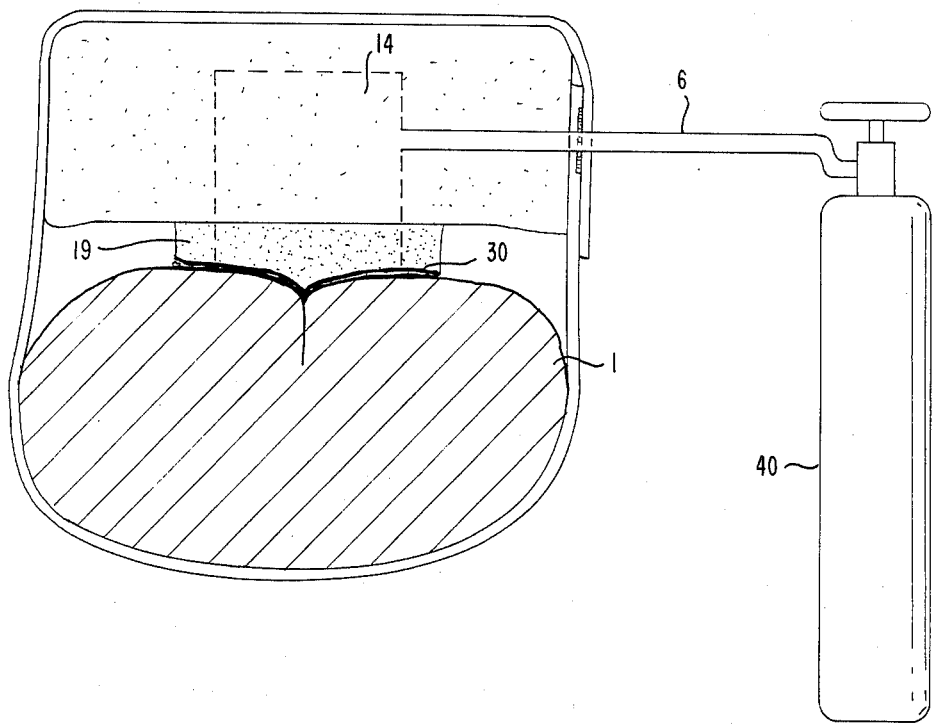
FIG. 6 is a side view of the hyperbaric chamber apparatus deposed on an irregularly shaped surface illustrating the apparatus's ability to conform.
Figure 5:
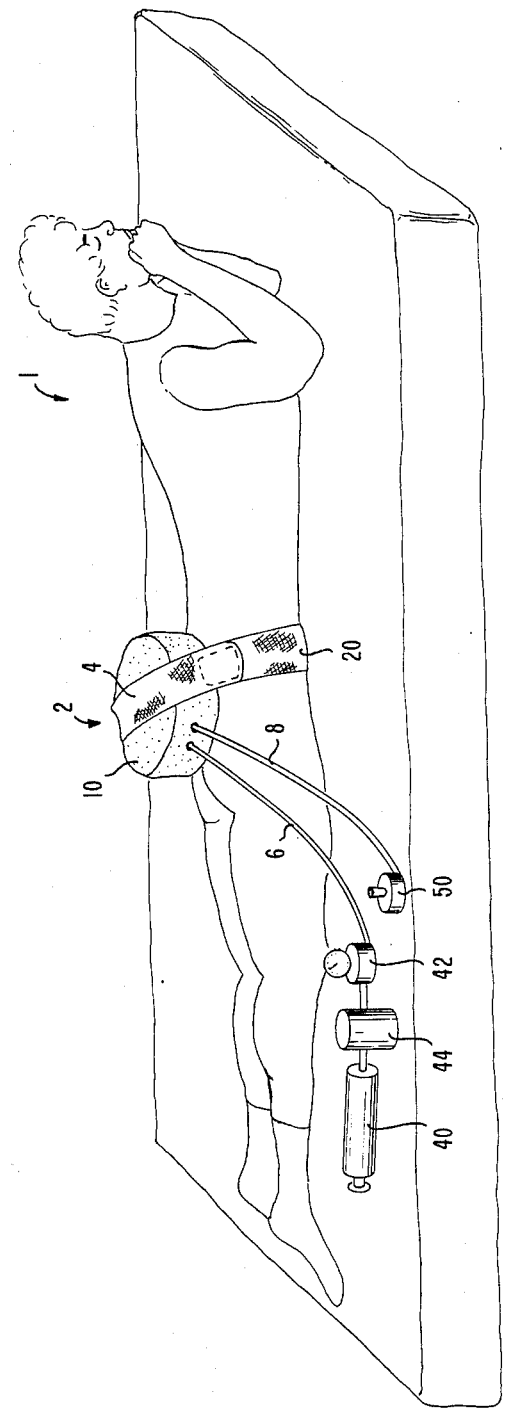
FIG. 5 illustrates a perspective and diagramatic view of the hyperbaric chamber apparatus in accordance with the present invention applied to a patient.

In a preferred embodiment of the present invention, shell 10, in conjunction with gas impermeable liner 12 and adhesive sealing material 30, is affixed to the patient's body so as to encapsulate within sealed chamber 14 a treatable lesion. Therapeutic gas source 40 is connected to this sealed chamber by therapeutic gas introduction means 6 and port 7. Therapeutic gases are then introduced within sealed chamber 14 by port 7. Such therapeutic gases pressurize sealed chamber 14 and ultimately pass by way of port 9 through pressure relief means 8 to pressure relief apparatus 50. Belt 20 is correspondingly wrapped around the patient's body 1 so as to reinforce and secure the sealed chamber 14 to the patient's body. As thus configured, the patient 1 need only ensure that therapeutic gas source 40 is introducing the therapeutic gases within the proper parameters by viewing control means 42. At that point, pressure relief apparatus 50 will ensure that the optimal conditions are maintained within the chamber itself. In this embodiment, pressure relief apparatus 50 is a static pressure relief valve. The atmosphere within sealed chamber 14 may also be moisturized by humidification means 44. FIGS. 5 and 6 illustrate the preferred method of application of the present invention. Hyperbaric chamber apparatus 2 is here affixed to the lower back in the region of the upper buttock, specifically in the region of the division between buttocks. In this figure, the hyperbaric chamber apparatus 2 is secured to the patient 1 by means of belt 20. Belt 20 is depicted as translucent, therefore, internal chamber 4 may be viewed within shell 10. Therapeutic gas introduction means 6 is attached to therapeutic gas source 40, humidification means 44, and control means 42. Pressure relief means 8 is here connected to pressure relief apparatus 50. In FIG. 6 protuberance 19 is seen as conforming with an irregularly shaped portion of the patient's body 1.

In this embodiment, shell 10 is preferably comprised of a polyurethane foam 32 and is conformable to the shape of the surface to which it is applied. Polyurethane foam 32 is characterized by a 1.4-pound density, a 34-pound indent load defamation, and is also fire retardant. Gas impermeable liner 12 may be any flexible and gas impermeable material, such material being well known, such as the occlusive poly film material manufactured by the 3M Corporation under the trademark BLEND DERM. Adhesive sealing means 30 is most preferably a hydrofluid material capable of repeated use and rejuvenation. Such adhesive means 30, for proper use, must also be hypoallergenic. Such characteristics are present in the adhesive material Karaya, a naturally occurring polymer resin.

As thus embodied, the present invention introduces an improved method of sealing which produces a hermetic seal. This improved method of sealing also produces numerous beneficial end results, such as portability, hermetic sealing in a portable device, the ability to treat previously untreatable wound sights, lower cost, and disposability.

The present invention, by creating a less complicated sealing means and hyperbaric apparatus, is extremely portable. The instant invention weighs in a preferred embodiment, less than 2 pounds, is small in size, and is easily transported. Also, because of its low pressure and volume requirements, the present invention allows for the use of the smaller and more portable E size oxygen cylinders. The prior hyperbaric chamber devices, such as Lo Piano, and Lasley, required the much larger H and K size cylinders. This is a significant advance. In addition, the present invention obviates the need for trained personnel for its application. This portability will also facilitate uses heretofore unavailable, such as uses in less accessible locations by people who would not usually have such apparatus available and will allow for patients receiving such treatment to have more normal lives and broader range of travel.

Not only will the present invention provide a portable hyperbaric chamber, as a result of adhesive sealing means 30 and the flexibility of shell 10, it also provides a portable hyperbaric chamber with the desired hermetic seal. This hermetic seal has many advantages. It allows for absolute control of the chamber's environment. Leaks which previously made control of the various parameters nearly impossible, will be greatly reduced. This hermetic seal will allow for the optimum conditions to be maintained within the chamber. The flow of the oxygen, the pressure of the oxygen, and the various other stimuli that are introduced within the chamber will be easily regulatable.

Also as a result of adhesive sealing material 30 and shell 10, the present invention also facilitates the treatment of wound sights previously untreatable in the absence of relatively sophisticated and cumbersome devices. For instance, lesions in the area of the buttock or bony protrusions of the hip are now treatable. This is particularly significant, because quite often treatable lesions occur in such areas. This device, with respect to such awkwardly placed lesions, will rival the effectiveness of more cumbersome and sophisticated machines.

Another dramatic result of the present invention is its lower manufacturing cost. The introduction of polyurethane foam 32 and adhesive sealing material 30 to the hyperbaric chamber environment facilitates the manufacture of a particularly useful device for a relatively low price. This will decrease end user cost and conversely increase end user use. As previously stated, this will enable many patients, who in the past were unable to afford such treatment, to now receive the proper therapy.

The lower manufacturing costs of the present device will produce wide ranging changes in the use of hyperbaric chambers. Hyperbaric chambers will become more widely available. For instance, a local drugstore which could not possibly afford to carry the previous embodiments of hyperbaric chambers, will be able to carry the present invention. Further, remote locations which may only store items which (1) are absolutely necessary, or (2) are affordable enough to keep one on hand just in case, will be able to stock the present invention.

The instant invention will also lead to wider use of hyperbaric chambers for the treatment of appropriate wounds. The "reluctant patient" will be much more likely to utilize a device which is low in cost and simple to use. The instant device, because of its low cost and ease of application as a result of adhesive sealing material 30, is particularly conducive to home treatment. The instant device's ease of application further reduces cost by not requiring application by a trained technician. Such ease of use will also facilitate wider use by allowing those physically incapable of applying the previous embodiments of portable hyperbaric chambers to apply the present invention by themselves.

The present invention will also allow for hyperbaric chamber treatments to be applied in area where it was previously inefficient and cost ineffective to do so. For instance, the treatment of minor wounds, such as burns, which would clearly heal over time and not require sophisticated treatment such as hyperbaric chamber treatment, will now be able to be healed faster by exposure to the hyperbaric atmosphere using the instant invention. Previously, such a course of treatment would have been cost ineffective and only available to those able to afford the finest of treatment. The present invention will allow many more people to receive hyperbaric healing treatments.

Another benefit which flows from such lower cost, is the ability to create a disposable hyperbaric chamber. This ability and result is significant and dramatic. There has been a significant need for such a disposable hyperbaric chamber in multi-patient health care facilities. In such facilities, there exists a considerable handicap in the use of hyperbaric chambers, namely, between each use, the device necessarily required sterilization. Further, there is always the risk of spreading the contagion of an infectious disease. These factors limited the availability of hyperbaric chamber atmosphere treatment.

With the relatively large investment required for institutions to purchase such devices, it was prohibitive to purchase enough devices to treat all patients as would optimally be required. This produces a situation in which patients are placed on waiting lists and required to take treatments as the devices become available. The present invention will allow the device to be purchased on a per-patient basis and, at the end of the patient's use, be disposed of or be taken home. This will allow more patients to obtain this treatment more frequently. For example, according to one study, thirty-eight percent of the patients in nursing homes have bedsores. As these types of devices are used today, those patients are required to wait until such equipment becomes available for their use. Because of the prohibitive costs, such patients may only be treated on a daily basis or less, rather than the twice daily optimum treatment schedule. The present device will allow for each patient to purchase their own hyperbaric chamber, which may be disposed of after use or be taken home when the patient is to be discharged.

The present invention, as previously mentioned, also simplifies the application and operation of such devices. Because the present invention is sealed by non-permeable liner 12, adhesive sealing material 30 and is secondarily reinforced by a belt 20, the patient is much more capable than previously possible to apply the instant device him or herself. Such ease of use will produce similar benefits to those created by lower cost and, in fact, make such benefits only more likely.

Although the invention herein has been described with reference to a specific embodiment, it is to be understood that this embodiment is merely illustrative of the principles and applications of the present invention. More specifically, it is to be understood that the embodiment, as represented in the detailed description of the present invention, is that embodiment which the inventor presently believes to be preferred. It is to be understood that numerous modifications may be made to the illustrative embodiment and that other arrangements may be devised from the spirit and scope of the present invention as defined by the appended claims.

What is claimed is:

1. A topical hyperbaric apparatus comprising:
    a shell having at least one wall providing an external surface and defining a substantially closed internal chamber, said at least one wall having an opening therethrough communicating with said internal chamber;
    adhesive sealing means provided on said external surface of said shell about said opening for adhesively sealing said shell to a patient's body about a portion to be treated; and
    gas introduction means for introducing therapeutic gases into said internal chamber for therapeutically treating the portion of the patient's body about which said shell is adhesively adhered.

2. The topical hyperbaric apparatus according to claim 1 wherein said opening is of a predetermined size sufficient to encompass the portion of the patient's body to be treated.

3. The topical hyperbaric apparatus according to claim 1 wherein said shell is substantially flexible.

4. The topical hyperbaric apparatus according to claim 3 wherein said shell is comprised of an open cell foam material.

5. The topical hyperbaric apparatus according to claim 1 further including a gas impermeable liner for lining said internal chamber for making said internal chamber substantially gas impermeable.

6. The topical hyperbaric apparatus according to claim 5 wherein said liner is substantially flexible.

7. The topical hyperbaric apparatus according to claim 1 wherein said adhesive sealing means comprises an adhesive polymer resin.

8. The topical hyperbaric apparatus according to claim 1 wherein said gas introduction means includes means for humidifying said therapeutic gases.

9. The topical hyperbaric chamber apparatus according to claim 1 wherein said gas introduction means includes pressure relief means for the maintenance of said therapeutic gases within said internal chamber.

10. The topical hyperbaric apparatus according to claim 9 wherein said pressure relief means comprises a static pressure relief valve.

11. The topical hyperbaric apparatus according to claim 1 further including a belting means adapted to be applied to the patient's body for positioning said shell.

12. The topical hyperbaric apparatus according to claim 1 wherein said at least one wall defines a protuberance extending outwardly from said chamber and wherein said opening is disposed within said protuberance.

13. The topical hyperbaric apparatus according to claim 12 wherein the size of said opening of said protuberance is sufficient to encompass the portion of the patient's body to be treated.

14. The topical hyperbaric apparatus according to claim 12 wherein said protuberance is substantially flexible.

15. The topical hyperbaric apparatus according to claim 14 wherein said protuberance is comprised of an open cell foam material.

16. The topical hyperbaric apparatus according to claim 14 wherein the size of said protuberance is sufficient to allow said protuberance to conform to an irregularly shaped surface.

17. A topical hyperbaric apparatus comprising:
    a shell having at least one wall providing an external surface and defining a substantially closed internal chamber, said at least one wall having an opening therethrough communicating with said internal chamber and further including at least one flexible wall portion circumscribing said opening, said at least one flexible wall portion being sufficiently flexible so as to be capable of conforming to an irregularly shaped surface of a patient's body;
    substantially gas impermeable means lining said internal chamber; and
    gas introduction means for introducing therapeutic gas into said internal chamber for therapeutically treating a portion of a patient's body.

18. The topical hyperbaric apparatus according to claim 17 wherein the size of said opening is sufficient to encompass the portion of the patient's body to be treated.

19. The topical hyperbaric apparatus according to claim 17 further comprising adhesive sealing means provided on said external surface of said shell about said opening for adhesively sealing said shell to a patient's body about a portion to be treated.

20. The topical hyperbaric apparatus according to claim 19 wherein said adhesive sealing means is comprised of an adhesive polymer resin.

21. The topical hyperbaric apparatus according to claim 17 wherein said shell is substantially flexible.

22. The topical hyperbaric apparatus according to claim 21 wherein said shell is comprised of an open cell foam material.

23. The topical hyperbaric apparatus according to claim 17 wherein said substantially gas impermeable means is substantially flexible.

24. The topical hyperbaric apparatus according to claim 17 wherein said gas introduction means includes means for humidifying said therapeutic gases.

25. The topical hyperbaric apparatus according to claim 17 wherein said gas introduction means includes pressure relief means for the maintenance of said therapeutic gases within said internal chamber.

26. The topical hyperbaric apparatus according to claim 25 wherein said pressure relief means comprises a static pressure relief valve.

27. The topical hyperbaric apparatus according to claim 17 further comprising a belting means adapted to be applied to the patients body for positioning said shell.

28. A topical hyperbaric apparatus comprising:
a shell having at least one flexible wall portion providing an external surface and defining a substantially closed internal chamber, said at least one wall having an opening therethrough communicating with said internal chamber and further including at least one flexible wall portion circumscribing said opening, said at least one flexible wall portion being sufficiently flexible so as to be capable of conforming to an irregularly shaped surface of a patient's body, said at least one flexible wall portion defining a protuberance extending outwardly from said internal chamber, said protuberance being disposed about said opening;
adhesive sealing means provided on said protuberance about said opening of said external surface of said shell for adhesively sealing said shell to a patient's body about a portion to be treated;
a gas impermeable liner for lining said internal chamber for making said internal chamber substantially gas impermeable; and
gas introduction means for introducing therapeutic gases into said internal chamber for therapeutically treating a portion of the patient's body to be treated.

29. A method of treating medical irregularities on a patient's body, which comprises the steps of:
providing a shell having at least one wall providing an external surface and defining a substantially closed internal chamber, said at least one wall having an opening therethrough communicating with said internal chamber, and adhesive sealing means provided on said external surface of said shell about said opening for adhesively sealing said shell to a patient's body about a portion to be treated;
affixing said hyperbaric apparatus to the portion of the patient's body to be treated with said adhesive sealing means; and
introducing therapeutic gases into said internal chamber to therapeutically treat the portion of the patient's body to be treated.

30. A method of treating medical irregularities on a patient's body, which comprises the steps of:
providing a topical hyperbaric apparatus which includes a shell having at least one wall providing an external surface and defining a substantially closed internal chamber, said at least one wall having an opening therethrough communicating with said internal chamber and further including at least one flexible wall portion circumscribing said opening, said at least one flexible wall portion being sufficiently flexible so as to be capable of conforming to an irregularly shaped surface of a patient's body, and a gas impermeable liner for of lining said internal chamber for making said internal chamber substantially gas impermeable;
placing said hyperbaric chamber apparatus on a portion of the patient's body so as to encompass a portion of the patient's body to be treated;
sealingly engaging said hyperbaric apparatus by causing said at least one flexible wall portion to sealingly conform to the patient's body by applying pressure in the direction of the patient's body; and
introducing therapeutic gases into said chamber and therapeutically treating the portion of the patient's body to be treated.

31. The apparatus according to claim 17 wherein said at least one flexible wall portion defines a protuberance extending outwardly from said chamber.

32. The apparatus according to claim 31 wherein said protuberance is comprised of an open cell foam material.

33. A topical hyperbaric apparatus comprising:
a shell having at least one wall providing an external surface and defining a substantially closed internal chamber, said at least one wall having an opening therethrough communicating with said internal chamber and further including a protuberance circumscribing said opening and extending outwardly from said chamber, said protuberance being sufficiently flexible so as to be capable of conforming to an irregularly shaped surface of a patient's body;
gas impermeable means for making said internal chamber substantially gas impermeable; and
gas introduction means for introducing therapeutic gas into said internal chamber for therapeutically treating a portion of a patient's body.

34. The topical hyperbaric apparatus according to claim 33 further comprising adhesive sealing means provided on said protuberance of said shell for adhesively sealing said shell to a patient's body about a portion to be treated.

35. The topical hyperbaric apparatus according to claim 34 wherein said adhesive sealing means is comprised of an adhesive polymer resin.

36. The topical hyperbaric apparatus according to claim 33 wherein at least said protuberance is comprised of an open cell foam material.

37. The topical hyperbaric apparatus according to claim 36 wherein said shell is comprised of an open cell foam material.

38. The topical hyperbaric apparatus according to claim 33 wherein said gas impermeable means comprises a gas impermeable liner for lining said internal chamber.

39. The topical hyperbaric apparatus according to claim 38 wherein said liner is substantially flexible.

40. The topical hyperbaric apparatus according to claim 33 wherein said gas introduction means includes means for humidifying said therapeutic gases.

41. The topical hyperbaric apparatus according to claim 33 wherein said gas introduction means includes pressure relief means for the maintenance of said therapeutic gases within said internal chamber.

42. The topical hyperbaric apparatus according to claim 41 wherein said pressure relief means comprises a static pressure relief valve.

* * * * *